United States Patent [19]

Blume et al.

[11] Patent Number: 5,389,447

[45] Date of Patent: Feb. 14, 1995

[54] POLYMERS OF 2,2-DISUBSTITUTED-3-HYDROXYPROPIONIC ACID FOR CERAMIC PROCESSING

[75] Inventors: Roe C. Blume; Lewis E. Manring; William G. Peet, all of Wilmington, Del.

[73] Assignee: E. I. Du Pont de Nemours and Company, Wilmington, Del.

[21] Appl. No.: 368,517

[22] Filed: Jun. 20, 1989

[51] Int. Cl.$^6$ .................... C08G 63/06; C04B 35/64
[52] U.S. Cl. .................... 428/480; 264/63; 501/1; 524/81; 524/539; 528/271; 528/361; 560/231; 562/579
[58] Field of Search ............... 528/361, 271; 562/579; 560/231; 524/81, 539; 428/480; 264/63; 501/1

[56] References Cited

U.S. PATENT DOCUMENTS

| | | |
|---|---|---|
| 2,952,877 | 9/1960 | Park, Jr. |
| 2,966,719 | 1/1961 | Park, Jr. |
| 4,613,648 | 9/1986 | Usala |
| 4,655,864 | 4/1987 | Rellick |

FOREIGN PATENT DOCUMENTS

| | | |
|---|---|---|
| 230664 | 10/1987 | Japan |
| 1190485 | 5/1970 | United Kingdom |
| 1323594 | 7/1973 | United Kingdom |

OTHER PUBLICATIONS

Lenz et al., "Ring–Opening Polymerization;" J. E. McGrath, Ed.; ACS Symposium Series 286; Am. Chem. Soc: Wash. D.C., 1985; p. 105 Sharkey, Ibid., p. 373.
Johns et al., "Ring–Opening Polymerization;" vol. 1, K. J. Ivin & T. Saegura, Eds.; Elsevier Appl. Sci. Publishers: New York, N.Y., 1984; Chap. 7.
Air Products and Chemicals, Inc., Product Information Bulletin.
R. W. Lenz et al., Polym. Eng. and Sci., 18, 937 (1978).

Primary Examiner—James Derrington

[57] ABSTRACT

Polymers of 2,2-disubstituted-3-hydroxypropionic acid, e.g., polymers of $\beta$-propiolactone, are employed in ceramic compositions as binders or dispersing agents.

20 Claims, No Drawings

POLYMERS OF 2,2-DISUBSTITUTED-3-HYDROXYPROPIONIC ACID FOR CERAMIC PROCESSING

FIELD OF THE INVENTION

This invention relates in general to polymeric binders, especially useful for producing castable ceramic compositions and to articles made therefrom, and to certain novel polymers and/or novel mixtures of polymers.

BACKGROUND OF THE INVENTION

Binders are employed in many ceramic compositions to provide the requisite green strength and plasticity for the shaping of the ceramic article prior to firing. Generally, the binder should volatilize readily, leaving essentially no residual ash during the firing, and ideally this decomposition should occur at less than 400° C. Furthermore, for certain purposes, binders should also volatilize and degrade cleanly in a nonoxidizing atmosphere, e.g., nitrogen, so that oxidizable metals such as copper, for example, will not oxidize during the fabrication of articles containing such metals, e.g., multilayer thick film circuits. In addition, it is advantageous for the binder to require little or no external plasticizer.

To obtain binders having such desired properties, extensive research on polymers has been conducted during the past fifty years. For example, in the past, various polymeric materials have been employed as the binder for green tapes, e.g., poly(vinyl butyral), poly(vinyl acetate), poly(vinyl alcohol), cellulosic polymers such as methyl cellulose, ethyl cellulose, hydroxy ethyl cellulose, methylhydroxy ethyl cellulose, atactic polypropylene, polyethylene, silicone polymers such as poly(methyl siloxane), poly(methyl phenyl siloxane), polystyrene, butadiene/styrene copolymer, polystyrene, poly(vinyl pyrrolidone), polyamides, high molecular weight polyethers, copolymers of ethylene oxide and propylene oxide, polyacrylamides, and various acrylic polymers such as sodium polyacrylate, poly(-lower-alkyl acrylates), poly(lower alkyl methacrylates) and various copolymers and multipolymers of lower alkyl acrylates and methacrylates. Copolymers of ethyl methacrylate and methyl acrylate and terpolymers of ethyl acrylate, methyl methacrylate and methacrylic acid have been previously used as binders for slip casting materials.

Representative references to polymeric binders are as follows:

U.S. Pat. No. 2,952,877 discloses a method of making ceramic a substantially water-soluble polymeric organic binder and a substantially water-soluble compatible organic plasticizer for said binder, with polyvinyl alcohol and triethyethylene glycol being preferred. Other binders are hide blue, alkali casein, dextrin, starch adhesives, polyacrylic acids, and polyacrylamide.

U.S. Pat. No. 2,966,719 discloses a compatibly plasticized thermoplastic binder resin, a preferred binder composition containing polyvinyl butyral (binder), polyalkylene glycol derivative (plasticizer), and an alkyl ether of polyethylene glycol (wetting agent). This patent also teaches how to manufacture thin ceramic films which may be handled in the same manner as tapes.

JP 62-230664 discloses the use of an isobutyl methacrylate copolymer with other vinyl monomers, having a glass transition temperature $(T_g) \leq 40°$ C. as a binder for ceramics. The use of this binder is said to minimize carbon retained in the fired ceramic thereby eliminating cracking and fissures in the ceramic product.

U.S. Pat. No. 4,613,648 discloses the use of an organic medium for the dispersion of inorganic solids containing as a binder a mixture of compatible polymers of methacrylates, acrylates, and an ethylenically unsaturated acid, said polymer having an $\overline{M}_w/\overline{M}_n$ no greater than 5.5. The $T_g$ of the polymer (and plasticizer therein, if any) is $-30°$ to $+45°$ C.

U.S. Pat. No. 4,655,864 discloses a polymeric binder selected from poly($\alpha$-methylstyrene) and polymers of methacrylate, for which the glass transition temperature of the polymer, including any plasticizer therein, is between $-30°$ and $+20°$ C. The binders are effective for nonoxidative firing in that they burn cleanly and thoroughly when fired at 825° to 1025° C.

Air products and Chemicals, Inc.; Product Information Bulletin discloses the use of poly(alkylene carbonates) for binders in ceramic applications. Poly(propylene carbonate) is said to differ from other ceramic binders in that it decomposes completely in air by 300° C. and by 360° C. in nitrogen. The glass transition temperature of the latter polymer is $+40°$ C.

Irrespective of the vast research that has been conducted, there is still a need for improved or alternative binders for the production of ceramics, and especially for the production of ceramic tapes.

SUMMARY OF THE INVENTION

A primary aspect of the present invention is directed to novel binder compositions for ceramic compositions, wherein binders consist essentially of polymers of 2,2-disubstituted-3-hydroxypropionic acid (hereinafter referred to as "3E polymers" because they are polyesters of a 3-carbon hydroxy acid), having glass transition temperatures in the range of $-10°$ to $+40°$ C. and volatilizing substantially cleanly at temperatures below 400° C., leaving low carbon residues.

According to another aspect of the invention, there are provided solutions of such binders, principally to facilitate the production of ceramic compositions.

A third aspect of the invention provides for compositions of the binder and particulate ceramic material.

A fourth aspect of the invention provides for shaped ceramic articles both in the green form, containing the binder, and in the fired form wherein the binder has been substantially volatilized.

A fifth aspect of the invention is directed to the above-shaped articles which are in the form of a tape, and a sixth aspect provides for an article of manufacture comprising the tape on a backing.

A seventh aspect of the invention is directed to a composition comprising a 3E polymer binder and a plasticizer which is other than a 3E polymer.

An eighth aspect of the invention provides for a slip composition comprising a 3E polymer binder, solvent, and particulate ceramic material.

A ninth aspect of the invention is directed to 3E polymers combined with organic ions that can catalyze degradation of the polymers and which are thermally stable at polymer degradation temperatures.

A tenth aspect of the invention is to provide slip and paste compositions wherein a 3E polymer is employed as a dispersing agent in conjunction with binders which are not 3E polymers.

Upon further study of the specification and appended claims, further aspects, objects and advantages of the invention will become apparent.

DETAILED DESCRIPTION OF THE INVENTION

Preferred 3E polymers directed to the aforesaid aspects are 3E polymers having a glass transition temperature ("$T_g$") of −30° to +40° C., preferably −10° to +20° C., and which degrade at temperatures below about 600° C., e.g., 200° to 400° C., in a helium atmosphere, leaving not more than approximately 250 ppm of carbon residues based on the weight of the 3E polymer. Such 3E polymers are also preferably substantially amorphous, e.g., having less than 10%, preferably less than 1%, crystallinity, if not completely amorphous. This substantially amorphous nature of the polymer is, preferably, also sufficiently stable to provide a satisfactory shelf life of the green products. For example, the green products should remain flexible for six months to two years.

In general, these 3E polymers are disubstituted at the 2-position by hydrocarbon substituents, particularly alkyl, cycloalkyl or aryl moieties. It is to be understood, moreover, that hetero atoms, e.g., oxygen and nitrogen, and functional groups, e.g., carboxy and halo may also be included in the polymers so long as they do not deleteriously affect the desired properties of the polymer.

A preferred subgeneric group of 3E polymers to be used as binders for the present invention are comprised of the same or different recurring units of:

$$\text{+CH}_2\text{CR}^1\text{R}^2\text{COO+}$$

wherein:
$R^1$ is $C_{1-4}$-alkyl or phenyl and preferably methyl;
$R^2$ is $C_{1-5}$-alkyl or phenyl, preferably $C_2$–$C_5$-alkyl, especially n-propyl or neopentyl.

It is likewise preferred that the above subgeneric group of polymers are substantially to entirely amorphous and/or melt below about 100° C., most preferably below about 30° C.

All of the random 3E copolymers which meet the following criteria are novel. The 3E copolymers have a $T_g$ below 40° C. and show no crystalline exotherm in differential scanning calorimetry (using a Mettler DSC differential scanning calorimeter in a temperature range of −100° C. to +150° C.). Thus, the novel polymers of this invention are quite different from the 3E copolymers of the examples in French Patent 1,231,163 (Kodak-Pathe Apr. 11, 1960) which are not only crystalline but also highly crystalline for the most part.

To obtain a binder composition of the correct properties, it is necessary to control the $T_g$ carefully. This can be accomplished by at least three methods. These include (1) addition of a structurally unrelated plasticizer, (2) addition of a 3E oligomer as plasticizer, and/or (3) avoidance of additives, by polymerization of a mixture of monomers selected to give a polymer of inherently correct $T_g$. The third method is generally preferred because there is no plasticizer to lose and the shelf life of the binder composition may therefore be expected to be years rather than the days, weeks or months experienced with composition produced by the first two methods.

It is possible for the $T_g$ of the binder polymer to be higher than +40° C., if it is mixed with a plasticizer to lower the $T_g$ of the binder. In any case, it is generally necessary for quite practical reasons of applicability that the glass transition temperature $T_g$ of the binder polymer including any plasticizer therein be at least −30° C. but no more than +40° C. It is preferred that the $T_g$ of the binder, including any plasticizer which it may contain, be from −10° C. to +20° C. When the $T_g$ is above 40° C., the final green ceramic body may be too brittle.

A particularly preferred binder is based on an equimolar terpolymer of methyl ethyl/methyl neopentyl/methyl propyl 2,2-disubstituted recurring units (3E units). Such a terpolymer has a glass transition temperature of about +7° C. and is noncrystalline.

Examples of mixtures of two recurring units are those of the above subgeneric group comprising the same or different repeating units, with at least one polymer being an oligomer having an average molecular weight of less than 5,000 and at least one polymer having an average molecular weight of about 10,000.

In general, the polymers of this invention have a weight average molecular weight of about 20,000 to 2,000,000, preferably 50,000 to 1,000,000.

As for the oligomers, they exhibit a degree of polymerization of 2 to 10, preferably 3 to 5.

The 3E polymers useful in this invention are preferably prepared by anionic polymerization (using tetraalkylammonium carboxylates as initiators) of α,α-disubstituted-β-propiolactones as disclosed by W. H. Sharkey in "Ring-Opening Polymerization"; J. E. McGrath, Ed.; ACS Symposium Series 286; American Chemical Society: Washington, D.C., 1985; p. 373 and references cited therein. The monomeric β-propiolactones, except for α-methyl-α-neopentyl-β-propiolactone (MNPL), are prepared by procedures described by D. B. Johns et al. in "Ring-Opening Polymerization"; Vol. 1, K. J. Ivin and T. Seagura, Eds.; Elsevier Applied Science Publishers: New York, N.Y., 1984; Chap. 7.

In addition to the polymerization of α,α-disubstituted-β-propiolactones, the 3E polymers of this invention can also be produced by the polymerization of the cyclic carbonate of 2,2-disubstituted-3-hydroxypropionic acid or of the free hydroxy acid itself.

MNPL is prepared by first reacting 2,4,4-trimethylpentene-1 with a source of peroxygen atoms, such as hydrogen peroxide, permaleic acid, perbenzoic acid, etc. The peracids are preferred since the intermediate epoxide is rearranged in situ by the parent acid to 2,4,4-trimethylpentanal. This aldehyde is then reacted with paraformaldehyde and glacial acetic acid to yield 2,4,4-trimethyl-2-acetoxypentanal. This latter aldehyde is oxidized to the acid with $KMnO_4$. The resultant acid is then converted to 2-methyl-2-neopentyl-3-hydroxypropionic acid by refluxing with aqueous NaOH followed by acidification with HCl. This acid is converted to MNPL by treatment with methyl orthopropionate under acid catalysis as described in U.S. Pat. No. 3,503,993. Whereas this preparation is not disclosed in D. B. Johns et al., supra, the MNPL polymer is disclosed in the reference on the eighth page of Table 7.4, third listed polymer. (In the aforesaid ACS symposium series 286, R. W. Lenz describes the preparation of poly(α-ethyl-α-n-butyl-β-propiolactone) having a bimodal molecular weight distribution with a $\overline{M}_w/\overline{M}_n$ of 2.24.)

Ceramic Compositions

The binder of the invention can be used with virtually any high melting inorganic solid material. Examples of ceramic compnents useful include, but are not limited to: cordierite, alumina, fired silica, quartz, anorthite, various glass frits, $BaTiO_3$, $CaTiO_3$, mullite, and $CaZrO_3$, as well as $BaZrO_2$, $SrTiO_3$, $PbTiO_3$, $MnO$, $Fe_2O_3$, $CaSnO_3$, $BaSnO_3$, $Bi_2O_3$, kyanite, forsterite, and zircon. The binder is particularly useful for making castable dispersions of dielectric solids such as cordierite and alumina. The particle size of the particulate ceramic is preferably in the range of 0.1 $\mu$ to 20 $\mu$, more preferably 0.5 $\mu$ to 5 $\mu$.

To obtain better binding efficiency, it is preferred to use about 1 to 20, preferably 5 to 10, parts by weight binder per 100 parts by weight of ceramic solids. The specific amount of binder in any given case will be dependent in part on the surface area of the ceramic solid particles. In general, high surface area ceramic solids will require higher amounts of the binder.

The organic medium in which the ceramic solids are dispersed comprises the polymeric binder dissolved in a volatile organic solvent and, optionally, other dissolved materials such as plasticizers, release agents, dispersing agents, thixotropic agents, stripping agents, antifouling agents and wetting agents.

It will be recognized that, by adjusting the rheological properties of the binder and by changing the solvent composition of the organic medium, the compositions of this invention can be applied to substrates by methods other than casting, e.g., by screen printing. When the compositions are applied by screen printing, the conventional organic media materials used for thick film materials can be used so long as the 3E polymers are completely soluble therein at application temperatures.

For casting dispersions, the solvent component of the organic medium is chosen so as to obtain a complete solution. It is also preferred that the solvent exhibit a sufficiently high volatility so that it can be evaporated from the dispersion by the application of relatively low levels of heat at atmospheric pressure. In addition, the solvent must boil well below the boiling point and decomposition temperature of any other additives contained in the organic medium. Thus, solvents having atmospheric boiling points below 150° C. are used most frequently. Such solvents include, but are not limited to: benzene, acetone, xylene, methanol, ethanol, methyl ethyl ketone, 1,1,1-trichloroethane, tetrachloroethylene, amyl acetate, toluene, methylene chloride, 2-propanol, and Freon ® TF (trichlorotrifluoroethane). Simple tests will determine the relative desirability of any given solvent for any given binder.

The total amount of organic binder, including any plasticizer which it may contain, must be high enough to obtain good lamination and high tape strength, but yet not so high as to decrease the packing of the dielectric particles. If too much organic material is contained in the green tape, sintering and densification on firing are likely to be inadequate. For these reasons, it is preferred that the volume of the binder (and plasticizer if one is used) be from 30 to 55% of the volume of the solvent-free green tape. From 40-50% volume is still more preferred.

As discussed hereinabove, the organic medium will also frequently contain a small amount, relative to the binder polymer, of a plasticizer, which serves to lower the $T_g$ of the binder polymer. However, the use of such materials should be minimized in order to increase shelf life. The choice of plasticizer is, of course, determined primarily by the polymer which must be modified. Among a host of plasticizers which can be used in various binder systems are especially diethyl phthalate, dibutyl phthalate, dioctyl phthalate, butyl benzyl phthalate, alkyl phosphates, polyalkylene glycols, glycerol, poly(ethylene oxides), hydroxyethylated alkyl phenol, dialkyldithiophosphonate, and poly(isobutylene). The amount of plasticizer used in the composition of the invention depends, of course, on the effectiveness of the particular plasticizer to reduce the $T_g$ of the polymer in which it is used as well as the relative degree of $T_g$ change which is required of the polymer in which it is used. Thus, the amount of plasticizer can generally vary from 0 to as high as 75% by weight of the polymer.

A particular aspect of the present invention comprises the use of 3E oligomers having a degree of polymerization of, for example, 2 to 10, preferably 3 to 5, with 3E polymers or copolymers which can serve as internal plasticizers thereby eliminating a contamination source when firing the ceramic composition.

Another aspect of the invention comprises the use of 3E polymers capped with selected terminal groups such as, for example, tetrabutyl phosphonium, which substantially lower the binder decomposition temperature, thus enabling the binders to be used with ceramic compositions which sinter at lower temperatures.

Since the 3E polymers of the present invention exhibit high dispersibility in the presence of ceramic particles, they also may be used as dispersants for both slips and pastes containing conventional binder systems, e.g., polyacrylates. For such purposes, the weight ratio of the 3E polymer to the ceramic solid binder is generally about 0.001:1 to 0.01:1, dependent on the surface area of the ceramic solids; in general, high surface area ceramic solids will require higher amounts of organics.

According to the invention, the binder can be used for the purposes of providing any green shape from any ceramic. The invention is particularly advantageous in connection with the production of green ceramic tape, especially such tape based on cordierite as the ceramic. Such ceramic green tapes are in general well known, reference being invited to, for example, Chapter 30 of the text "Ceramic Processing Before Firing," Editors G. Y. Onoda and L. L. Hench (Wiley, New York, 1978, pages 411–448). Note, in particular, that tapes are generally less than $\frac{1}{8}$ inch in thickness, with the most benefit being provided in the 1–50 mil range. It is further noted that the substrate is most often a metal belt or a plastic film made of Mylar, polyethylene or the like, or in some cases individual glass plates. Green tapes made in accordance with the present invention exhibit enhanced strength and flexibility.

In addition, the fired ceramic shapes made in accordance with this invention exhibit improved properties from the standpoint of low residual carbon as well as improved electrical properties, higher density and lower porosity than fired products made with other binders.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all termperature are set forth uncorrected in degrees Celsius and unless otherwise indicated, all parts and percentages are by weight, except for percentages of monomeric units in copolymers which are expressed in mole percent of units found in the final copolymer.

The entire texts of all patents and publications cited above and below are hereby incorporated by reference.

Experimental $^1$H NMR spectra were recorded on a spectrometer and chemical shifts are reported relative to tetramethylsilane at 0 ppm. NMR spectra were recorded on a General Electric QE-300 NMR Spectrometer operating at 300 Hz. Infrared spectra were recorded on a Perkin-Elmer 983G Infra Red Spectrometer.

Gas chromatography was done using a Hewlett-Packard HP5710A Gas Chromatograph equipped with a 6'×⅛" stainless steel column packed with 10% SP-2100 on 80/100 Supelcoport and using He carrier gas operating at 75° C./1 min, then programmed at 16°/min to 250° C.

Dielectric Constant (K) is a measure of the ability of a dielectric material to store an electrical potential energy under the influence of an electrical field. Thus, it is the ratio between the capacitance of a capacitor with the subject material as dielectric (the fired dielectric in this case) to the capacitance of a capitor with a vacuum as the dielectric.

Porosity of the fired ceramics was determined using ASTM Method F 97-72 with Zyglo® dyes.

Archimedes' density was determined by first weighing the dry sample in air; second, the sample was weighted again while being suspended in a solution of known density, e.g., distilled water, containing a drop of a surfactant; and lastly, using the following equation:

Density (g/cc)=Dry weight/[Dry weight−Weight
in water] to calculate the density.

Weight- and number-average molecular weights ($\overline{M}_w$ and $\overline{M}_n$) were determined by gel permeation chromatography (GPC). Oligomer molecular weights were determined using vapor pressure osmometry.

Preparation of α-Methyl-α-neopentyl-β-propiolactone a. Preparation of
2-methyl-2-neopentyl-3-acetoxypropionic acid (1.)

To an ice-cooled 2 L flask equipped with a mechanical stirrer was added 2,2,4-trimethyl-2-acetoxy-pentanal (162 g, 0.81 mol), glacial acetic acid (750 mL), and 85% phosphoric acid (100 mL). To this solution was added dropwise KMnO$_4$ (922 g, 0.58 mol) in water (600 mL) at such a rate to maintain the reaction temperature at 15°-20° C. At the end of the permanganate addition, NaHSO$_3$ (100 g) in water (200 mL) was added, followed by dilution with water (1.2 L), and extraction several times with ether and benzene (300 mL). Drying and evaporation followed by recrystallization from hexane afforded 2-methyl-2-neopentyl-3-acetoxypropionic acid (1) (100 g, 57% yield), m.p. 89.5°-90.5° C. $^1$H NMR (CDCl$_3$): 0.97 (s, 9H), 1.30 (s, 3H), 1.52, 1.77 (AB, 2H), 2.06 (s, 3H), 4.05, 4.20 (AB, 2H), 11.5 (broad s, 1H).

b. Preparation of
2-methyl-2-neopentyl-3-hydroxypropionic acid (2.)

In a 100 mL 3-necked RB flask, acid (1) (4.8 g, 0.022 mol) was stirred at reflux with a solution of sodium hydroxide (4.0 g) in water (40 mL) for 20 hours. The mixture was cooled and acidified with concentrated HCl. After drying, there was obtained 2-methyl-2-neopentyl-3-hydroxypropionic acid (2) (3.2 g, 85% yield), m.p. 96.5°-100° C.; recrystallized from n-hexane, m.p. 99°-101° C. $^1$H NMR (CDCl$_3$): 0.97 (s, 9H), 1.31 (s, 3H), 1.74, 1.54 (AB, 2H), 3.88, 3.40 (AB, 2H), ca. 6.75 (s broad, 2H).

c. Preparation of
α-methyl-α-neopentyl-β-propiolactone

The resultant 2-methyl-2-neopentyl-3-hydroxypropionic acid (2.) was then reacted conventionally with methyl orthopropionate, followed by slow heating in the presence of Amberlyst® 15, then worked up to obtained the desired final product.

For the following examples and during the course of research leading to the invention, a variety of homopolymers and copolymers were produced, as exemplified by the following homopolymerization in Example A and copolymerization reaction in Example B:

Example A

2-Methyl-2-neopentyl-3-propiolactone (1.56 g), tetrahydrofuran (10 mL) and initiator solution (50 μL, containing 2×10$^{-4}$ mole tetrabutylammonium pivalate per mL toluene) were added to a vial and stirred and heated at 65° C. for one hour. At that point, infrared (IR) analysis showed the complete absence of a peak at 1825 cm$^{-1}$ which is a characteristic peak for β-propiolactone. The solvent was then removed by steam distillation and the polymer dried in air. The inherent viscosity (I.V.) was determined for a 0.1 g/10 mL solution in CH$_2$Cl$_2$ as 0.353 dl/g.

Example B

To a stirred solution of 2-methyl-2-neopentyl-3-propiolactone (124.8 g, 0.8 mole) and 2-methyl-2-propyl-3-propiolactone (25.6 g, 0.2 mole) in tetrahydrofuran (800 mL) at room temperature was added tetrabutylammonium hydroxide in methanol (350 μL of a 1.0N solution). The clear solution was then heated to reflux for 3.75 h when IR analysis showed no lactone absorption at 1825 cm$^{-1}$. The solvent was removed by steam distillation followed by polymer drying in a vacuum oven at 29" Hg and 70° C. The inherent viscosity (I.V.) was determined for a 0.1 g/10 mL solution in CH$_2$Cl$_2$ as 1.033 dl/g.

Properties of particular homopolymers of the subgeneric group of 3E polymers described above are tabulated below in Table A.

TABLE A

| Data on 3E Polymers; $T_g$, $T_m$ and Crystallinity | | | | | |
|---|---|---|---|---|---|
| $R_1$ | $R_2$ | $T_g$ | $T_m$ | % Crystallinity | Reference |
| CH$_3$ | CH$_3$ | 17 | 240 | 80 | (1) |
| CH$_3$ | C$_2$H$_5$ | −13 | 122 | low | (1) |
| CH$_3$ | n-C$_3$H$_7$ | 0 | −100 | low 20 | (1) |
| CH$_3$ | n-C$_4$H$_9$ | −13 | 40–50 | low | (1) |
| CH$_3$ | n-C$_5$H$_{11}$ | ? | 54 | ? | (1) |
| CH$_3$ | neo-C$_5$H$_{11}$ | 54 | — | — | |
| C$_2$H$_5$ | C$_2$H$_5$ | 10 | −225 | 17 | (1) |

(1) D. B. Johns, R. W. West and A. Luecke in "Ring-Opening Polymerizations", Chapter 7, Lactones; K. J. Ivin and T. Saegusa Eds., Elsevier 1984.

Properties of methyl propyl/methyl neopentyl 3E copolymers, and methyl propyl/methyl neopentyl/methyl ethyl 3E terpolymers of the subgeneric group of 3E polymers described above are tabulated in Tables B and C, respectively.

TABLE B

Properties of Methyl propyl (MP)/Methyl neopentyl (MN) Copolymers

| % MP | % MN | $T_g$ | $T_m$ |
|---|---|---|---|
| — | 100 | 54° C. | — |
| 10 | 90 | 48° C. | — |
| 20 | 80 | 40° C. | — |
| 40 | 60 | 34° C. | — |
| 60 | 40 | 20° C. | — |
| 80 | 20 | 8° C. | 50 & 80 |
| 100 | — | 4° C. | 90° C. |

TABLE C

Properties of Methyl propyl (MP)/Methyl neopentyl (MN)/Methyl ethyl (ME) Terpolymer

| % MP | % MN | % ME | $T_g$ | $T_m$ |
|---|---|---|---|---|
| 33 | 33 | 33 | 5° C. | — |
| 25 | 50 | 25 | 8° C. | — |
| 25 | 25 | 50 | 4° C. | 56° C. |
| 50 | 25 | 25 | 4° C. | — |
| 100 | 0 | 0 | 4° C. | 90° C. |
| 0 | 100 | 0 | 54° C. | — |
| 0 | 0 | 100 | −13° C. | 122° C. |

In the following examples, the Cordierite (Specialty Glass—SP980) and Cordierite (Pemco) are commercially available. Also, the polymers are all species of the above-described subgeneric formula of 3E polymers. The inherent viscosities (I.V.) in dl/g are determined for a 0.1 g/10 mL solution in $CH_2Cl_2$, at 25° C., for examples 1–9, and the same for examples 10–13 except that tetrahydrofuran is employed as the solvent.

EXAMPLE 1

Three Component 3E Terpolymer/Cordierite Slip, Tape and Laminate Fabrication

A ceramic slip was prepared by ball milling the following constituents for 18 hours:
  40.0 g Cordierite (Specialty Glass—SP980)
  6.0 g Methyl ethyl (1 part)/methyl propyl (1 part)-/methyl neopentyl (1 part) 3E Terpolymer (Inherent viscosity ("I.V.")=1.215)
  57.0 mL 1,1,1-Trichloroethane The polymer was dissolved in the solvent prior to ball milling. After ball milling, a ceramic slip was cast onto a Mylar ® (DuPont, polyester film) tape (25 mil wet cast) to yield a dry 8 mil tape, which exhibited excellent flexibility and green strength and was peeled easily from the Mylar ®. The green tape exhibited a Young's Modulus, measured by the method described in ASTM Method D638-87b, of 78.06 MPa, an elongation at break of 37.9% and a toughness, measured by the method described in ASTM Method D638-87b, of 0.438 MPa. The Mylar ® backing was removed and a six layer laminate was fabricated from this green tape at 70° C. and 68.9 MPa for 5 minutes. The laminate was then fired at 4° C./min. to 400° C. and held at this temperature for 4 hours to remove binder. This was followed by sintering at 10° C./min. to 950° C. and holding at this temperature for 2 hours.

Based on the Zyglo ® dye test, the sample was nonporous. The density (Archimedes) was 2.61 g/cc. Shrink in the x and y direction was 22%, in the z direction (thickness), shrink was 20%.

EXAMPLE 2

Methyl neopentyl (80%)/Methyl propyl (20%) 3E Copolymer/Cordierite Slip, Tape and Laminate Fabrication A ceramic slip was prepared by ball milling the following constituents for 18 hours:
  40.0 g Cordierite (Specialty Glass—SP980)
  5.05 g Methyl propyl (20%)/methyl neopentyl (80%) 3E Copolymer (I.V.=1,808)
  1.25 g Flexol ® CC-55 plasticizer (bis-2-ethylhexyl hexahydrophthalate Union Carbide)
  65 mL 1,1,1-Trichloroethane The polymer and plasticizer were dissolved in the solvent prior to ball milling. After ball milling, a ceramic slip was cast onto a Mylar ® tape (15 mil wet cast) to yield a very flexible and stretchable green tape. The green tape exhibited a Young's Modulus of 149.3 MPa, an elongation at break of 42.7 and a toughness of 0.392 MPa. The Mylar ® backing was removed and an eight layer laminate was prepared from this tape at 70° C. and 68.9 MPa for 5 minutes. The laminate was then fired at 4° C./min. to 400° C. and held at this temperature or 4 hours to remove binder. This was followed by sintering in air at 10° C./min. to 1000° C. and holding at this temperature for 2 hours.

Shrink in the x and y direction was 20%, in the z direction (thickness), shrink was 20%.

EXAMPLE 3

Methyl neopentyl (90%)/Methyl propyl (10%) 3E Copolymer/Cordierite Slip, Tape and Laminate Fabrication A ceramic slip was prepared by ball milling the following constituents for 21 hours:
  40.0 g Cordierite (Specialty Glass—SP980)
  3.12 g Methyl propyl (10%)/methyl neopentyl (90%) 3E Copolymer (I.V.=0.797)
  3.12 g Methyl neopentyl oligomer (D.P.=4.0)
  37 mL 1,1,1-Trichloroethane The polymer and oligomer were dissolved in the solvent prior to ball milling. After ball milling, a ceramic slip was cast onto a Mylar ® tape (20 mil wet cast) to yield a green tape which remained flexible for 32 days. The Mylar ® backing was removed and a six layer laminate was prepared from this tape at 70° C. and 68.9 MPa for 5 minutes. The laminate was then fired at 4° C./min. to 400° C. and held at this temperature for 4 hours to remove binder. This was followed by sintering in air at 10° C./min. to 1000° C. and holding at this temperature for 2 hours.

Shrink in the x and y direction was 24%, in the z direction (thickness), shrink was 21%. The sample was nonporous based on the Zyglo ® dye test.

EXAMPLE 4

Methyl neopentyl (80%)/Methyl propyl (20%) 3E Copolymer/Cordierite Slip, Tape and Laminate Fabrication A ceramic slip was prepared by ball milling the following constituents for 21 hours:
  40.0 g Cordierite (Specialty Glass—SP980)
  3.12 g Methyl propyl (20%)/methyl neopentyl (80%) 3E Copolymer (I.V.=1.165)
  3.12 g Methyl neopentyl oligomer (D.P.=4.0)
  47 mL 1,1,1-Trichloroethane The polymer and oligomer were dissolved in the solvent prior to ball milling. After ball milling, a ceramic slip was cast onto a Mylar ® tape (20 mil wet cast) to yield a green tape which remained flexible for 32 days. The Mylar ® backing was removed and a six layer laminate was prepared from this tape at 70° C. and 68.9 MPa for 5 minutes. The laminate was then fired at 4° C./min. to 400° C. and held at this temperature for 4 hours to remove binder. This was followed by sintering in air at 10° C./min. to 1000° C. and holding at this temperature for 2 hours.

Shrink in the x and y direction was 25%, in the z direction (thickness), shrink was 22%. The sample was nonporous based on the Zyglo ® dye test.

EXAMPLE 5

Methyl neopentyl (60%)/Methyl propyl (40%) 3E Copolymer/Cordierite Slip, Tape and Laminate Fabrication A ceramic slip was prepared by ball milling the following constituents for 21 hours:
40.0 g Cordierite (Specialty Glass—SP980)
3.12 g Methyl propyl (40%)/Methyl neopentyl (60%) 3E Copolymer (I.V.=1.084)
3.12 g Methyl neopentyl 3E Oligomer (D.P.=4.1)
39 mL 1,1,1-Trichloroethane The polymer and oligomer were dissolved in the solvent prior to ball milling. After ball milling, a ceramic slip was cast onto a Mylar ® tape (20 mil wet cast) to yield a green tape which remained flexible for 32 days. The Mylar ® backing was removed and a six layer laminate was prepared from this tape at 70° C. and 68.9 MPa for 5 minutes. The laminate was then fired at 4° C./min. to 400° C. and held at this temperature for 4 hours to remove binder. This was followed by sintering at 10° C./min. to 1000° C. and holding at this temperature for 2 hours.

Shrink in the x and y direction was 24%, in the z direction (thickness), shrink was 27%.

EXAMPLE 6

Methyl neopentyl (80%)/Methyl propyl (20%) 3E Copolymer/Cordierite Slip, Tape and Laminate Fabrication A ceramic slip was prepared by ball milling the following constituents for 18 hours:
40.0 g Cordierite (Specialty Glass—SP980)
4.1 g Methyl propyl (20%)/Methyl neopentyl (80%) 3E Copolymer (I.V.=0.979)
2.2 g Methyl neopentyl 3E Oligomer (D.P.=2.4)
45 mL 1,1,1-Trichloroethane The polymer was dissolved in the solvent, then the oligomer prior to ball milling. After ball milling, a ceramic slip was cast onto a Mylar ® tape (20 mil wet cast) to yield a green tape which remained flexible for at least 10 days. The green tape exhibited a Young's modulus of 73.6 MPa, an elongation at break of 34.9% and a toughness of 0.33 MPa. The Mylar ® backing was removed and a six layer laminate was prepared from this tape at 70° C. and 68.9 MPa for 5 minutes. The laminate was then fired at 4° C./min. to 400° C. and held at this temperature for 4 hours to remove the binder. This was followed by sintering in air at 10° C./min. to 1000° C. and holding at this temperature for 2 hours.

Shrink in the x and y direction was 22%, in the z direction (thickness), shrink was 18%. The sample was nonporous based on the Zyglo ® dye test.

EXAMPLE 7

Methyl neopentyl 3E Oligomer/Cordierite Slip, Tape and Laminate Fabrication

Methyl neopentyl 3E oligomer having a D.P. of 4.1 (0.5 g) was dissolved in trichloroethane (140 mL). Cordierite (80.0 g) was added to this solution, stirred for 5 minutes, followed by adding a solution of Elvacite ® 2010 (DuPont, polymethyl methacrylate) (6.25 g) dissolved in 1,1,1-trichloroethane (30 mL) which also contained Santicizer ® 160 (Monsanto, benzyl butyl phthalate) (6.25 g) plasticizer which had been added to the Elvacite ® solution. After overnight stirring at room temperature (RT), the dispersion was sonicated at 40% power for 5 minutes followed by refluxing the solvent with stirring for 4 hours. Trichloroethane (ca. 100 mL) was then removed by distillation. The resulting slip, after cooling to RT, was filtered through a −385 mesh screen to remove large agglomerates. The dispersion thus obtained was cast onto Mylar ® film at the rate of 15 feet/minute. The green tape exhibited a Young's Modulus of 33.4 MPa, an elongation at break of 20.2% and a toughness of 0.066 MPa. The Mylar ® backing was removed and two ten-layer laminates were prepared from this tape at 70° C. and 68.9 MPa for 5 minutes. The laminates were then fired at 4° C./min. to 400° C. and held at this temperature for 4 hours to remove binder. This was followed by sintering at 10° C./min. to 1000° C. and holding at this temperature for 2 hours.

The average shrink in the x and y direction was 20.0%, in the z direction (thickness), shrink was 16.5%. The Archimedes' density of the ceramics was 2.59 g/mL (99.6% dense). The dielectric constant measured on a Hewlett-Packard Model 4275A LCR Meter was at a frequency of 1 MHz was 5.27 K.

EXAMPLE 8

Methyl neopentyl 3E Polymer/Methyl neopentyl 3E Oligomer/Cordierite Slip, Tape and Laminate Fabrication Methyl neopentyl 3E polymer (6.25 g), having an I.V. of 0,695, and methyl neopentyl 3E oligomer (6.25 g), having a D.P. of 4.1, were dissolved in trichloroethane (150 mL). Cordierit ® (80.0 g) was slowly added to this solution and stirred slowly at RT for 17 hours. The slurry was heated under reflux for one hour followed by the removal of trichloroethane (ca. 75 mL) by distillation. The resulting slip, after cooling to RT, was filtered through a −385 mesh screen to remove large agglomerates. The dispersion thus obtained was cast onto Mylar ® film in wet thicknesses of 20, 25 and 30 mil. The green tape (average of five measurements) exhibited a Young's modulus of 71.1 MPa, an elongation at break of 10.48% and a toughness of 0.045 MPa. The dry thicknesses of the above tapes were 6, 7.5, and 9 mil. respectively. The Mylar ® backing was removed and a ten-layer laminate was prepared from the 7.5 mil. tape at 70° C. and 68.9 MPa for 5 minutes. The laminate was then fired at 4° C./min. to 400° C. and held at this temperature for 4 hours to remove binder. This was followed by sintering at 10° C./min. to 1000° C. and holding at this temperature for 2 hours.

The average shrink in the x and y direction was 18%, in the z direction (thickness), shrink was 25%. The Archimedes' density of the ceramics was 2.58 g/cc. The dielectric measurement at 1 MHz was 5.362 K.

EXAMPLE 9

Methyl neopentyl 3E Polymer/Methyl neopentyl 3E Oligomer/Cordierite Slip, Tape and Laminate Fabrication A ceramic slip was prepared by ball milling the following constituents for 18 hours:
80.0 g Cordierite (Specialty Glass—SP980)
5.5 g Methyl neopentyl 3E Polymer (I.V.=695)
5.5 g Methyl neopentyl 3E Oligomer (D.P.=4.1)
55 mL 1,1,1-Trichloroethane The polymer and oligomer were dissolved in the solvent prior to ball milling. After ball milling, the ceramic slip was cast onto a Mylar ® tape (20 mil wet cast) to yield a green tape which exhibited good flexibility and strength. The Mylar ® backing was removed and a four layer laminate was prepared from this tape at 70° C. and 68.9 MPa for 5 minutes. The laminate was then fired at 4° C./min. to 400° C. and held at this temperature for 4 hours to remove binder. This was followed by sintering at 10° C./min. to 1000° C. and holding at this temperature for 2 hours.

Shrink in the x and y direction was 22%, in the z direction (thickness), shrink was 14%. The Archimedes' density of the ceramic was 2.59 g/cc.

EXAMPLE 10

Methyl neopentyl 3E Polymer/Methyl neopentyl 3E Oligomer/Cordierite Slip, Tape and Laminate Fabrication A ceramic slip was prepared by ball milling the following constituents for 21 hours:
80.0 g Cordierite (Pemco)
3.75 g Methyl neopentyl 3E Polymer (I.V.=0.134)
3.62 g Methyl neopentyl 3E Oligomer (D.P.=4.1)
7.93 mL Methylene chloride
25.4 mL 1,1,2,2-Tetrachloroethylene The polymer and oligomer were dissolved in the solvents prior to ball milling. After ball milling, a ceramic slip was cast onto a Mylar ® tape (10 and 20 mil wet cast) to yield flexible green tapes. Samples of the tapes, after removal of the Mylar ® backing, were fired at 2° C./min. to 400° C. and held at this temperature for 6 hours. This was followed by sintering at 10° C./min. to 1000° C. and holding at this temperature for 4 hours. The ceramic parts obtained by this procedure were dense. Samples of the tapes were fired also in nitrogen under the same conditions except that the sintering was done at 2° C./min. The resulting parts exhibited a slight porosity based on a Zyglo ® dye test.

EXAMPLE 11

Methyl neopentyl 3E Polymer/Cordierite Slip and Tape Fabrication

A ceramic slip was prepared by ball milling the following constituents for 4 hours and 20 hours:
80.0 g Cordierite (Pemco)
3.75 g Methyl neopentyl 3E Polymer (I.V.=635)
3.62 g Santicizer ® 160
7.93 mL Methylene chloride
25.4 mL 1,1,2,2,-Tetrachloroethylene After ball milling, ceramic slips were cast onto a Mylar ® tape (10 and 20 mil wet cast) to yield four green tapes. Samples of the four tapes, after removal of the backing, were fired at 2° C./min. to 400° C. and held at this temperature for 202 hours. This was followed by sintering at 4° C./min. to 950° C. and holding at this temperature for 3 hours. All of the resulting ceramics were found to be nonporous based on the Zyglo ® dye test.

EXAMPLE 12

Methyl neopentyl 3E Polymer/Cordierite Slip and Tape Fabrication

A ceramic slip was prepared by ball milling the following constituents for 21 hours:
80.0 g Cordierite (Pemco)
3.75 g Methyl neopentyl 3E Polymer (I.V.=0.360)
3.62 g Santicizer ® 160
7.93 mL Methylene chloride
25.4 mL 1,1,2,2-Tetrachloroethylene The polymer was dissolved in the solvents prior to ball milling. After ball milling, a ceramic slip was cast onto a Mylar ® tape (10 and 20 mil wet cast) to yield two green tapes. Samples of the tapes, after removal of the backing, were fired at 2° C./min. to 400° C. and held at this temperature for 6 hours. This was followed by sintering at 10° C./min. to 950° C. and holding at this temperature for 4 hours. Both of the resulting ceramics were found to be nonporous based on the Zyglo ® dye test.

EXAMPLE 13

Methyl propyl 3E Polymer/Cordierite Slip and Tape Fabrication

A ceramic slip was prepared by ball milling the following constituents for 3 hours and 21 hours:
80.0 g Cordierite (Pemco)
3.75 g Methyl propyl 3E Polymer (I.V.=0,490)
2.62 g Santicizer ® 160
7.93 mL Methylene chloride
25.4 mL 1,1,2,2-Tetrachloroethylene The polymer was dissolved in the solvents prior to ball milling. After ball milling, a ceramic slip was cast onto a Mylar ® tape (10 and 20 mil wet cast) to yield four green tapes. Samples of the four tapes, after removal of the backing, were fired at 2° C./min. to 400° C. and held at this temperature for 20 hours. This was followed by sintering at 4° C./min. to 950° C. and holding at this temperature for 3 hours. All of the resulting ceramics were found to be nonporous based on the Zyglo ® dye test.

EXAMPLE 14

Ion-Exchange of End Groups Effects on the the Thermal Degradation of Poly($\alpha$-methyl-$\alpha$-n-propyl-$\beta$-propiolactone) (MPPL or Methyl n-propyl 3E polymer)

a. Purification and Protonation of MPPL

MPPL ($M_w$=121,000; $M_n$=115,000) containing tetrabutylammonium carboxylate end groups was prepared by known methods, e.g., the procedure described in R. W. Lenz, ACS Symposium Series, 286, 105 (1985). For each gram of polymer, tetrahydrofuran (THF, 5 mL) and acetic acid (1 g) were added to effect solution of the polymer. While stirring the solution, distilled water (2 mL/mL tetrahydrofuran (THF)) was added. The polymer precipitate which now has carboxylic acid terminated end groups was collected in a Buchner funnel and washed with a large excess of water 7 to 8 times. After water removal, the polymer was dried either in a 70° C. oven or under reduced pressure.

b. Formation of Alkali Ion Exchanged Terminated Polymers

Stock alkali hydroxide base solutions were prepared in water which were 1N in Li, Na, or K ions, or 0.5N in Cs ion. The protonated polymer was dissolved in THF (1 g polymer/3 mL THF) and 100 μL of the stock base solution added. After stirring for 10 minutes, water (10 mL) was slowly added. The polymer precipitate was collected and washed with a large excess of distilled water. Gel permeation chromatography indicated a $\overline{M}_w$ of 120,000 for the carboxylic acid terminated polymer and 126,000 for the cesium terminated polymer; which shows that ion exchange was not degrading the polymer. Microanalysis of the polymer samples revealed that the carboxylate end groups were 88, 75, 100, and 20% exchanged respectively by $Li^+$, $Na^+$, $K^+$ and $CS^+$ using the above procedure.

c. Thermal Gravimetric Analysis (TGA) of Ion Exchanged Polymers

The results of TGA analysis at a heating rate of 10° C./min in nitrogen are shown in Table 1.

TABLE 1

Thermal Degradation of Ion Exchanged Polymer

| Polymer | Cation | Peak Degradation |
|---|---|---|
| MPPL-COOH | $H^+$ | 409° C. |
| MPPL-COOLi | $Li^+$ | 369° C. |
| MPPL-COONa | $Na^+$ | 365° C. |
| MPPL-COOK | $K^+$ | 352° C. |
| MPPL-COOCs | $Cs^+$ | 341° C. | d. Effect of Added Tetrabutylphosphonium Acetate (TBPA) on the Thermal Degradation of MPPL Solutions of TBPA in THF were prepared by adding the appropriate amount of 70% TBPA in methanol to THF or by serial dilutions of more concentrated solutions. The TBPA solutions were 0.05, 0.02, 0.01, 0,005, 0.0025, 0.0013, 0.0006, 0.0003, and 0.00015M in THF. Polymer samples were prepared by dissolving carboxylic acid terminated polymer (100 mg), prepared as described above, in TBPA/THF solution (1 mL). Removal of the THF gave polymer with the desired amount of TBPA in it. TGA analysis of these samples are shown in Table 2.

TABLE 2

Thermal Degradation of MPPL-COOH with TBPA Added

| TBPA Sol. | Peak Degradation |
|---|---|
| 0.05M | 230° C. |
| 0.02 | 240° C. |
| 0.01 | 250° C. |
| 0.005 | 270° C. |
| 0.0025 | 290° C. |
| 0.0013 | 350° C. |
| 0.0006 | 420° C. |
| 0.0003 | 420° C. |
| 0.00015 | 430° C. |

EXAMPLE 15

Carbon Residues After Firing Binders in $N_2$

Five binder solutions were prepared as shown:

(A) Ethyl cellulose N-22 grade (Hercules) (1.1 g) was dissolved in Texanol ® (Eastman Chemical Products, Inc.) (2,2,4-trimethyl-1,3-pentanediol monoisobutyrate) (8.9 g).

(B) Ethyl cellulose N-50 grade (1.1 g) was dissolved in Texanol ® (8.9 g).

(C) Poly(α-methyl-α-n-propyl-β-propiolactone) (MPPL) (1.1 g) was dissolved in Texanol ® (8.9 g).

(D) Poly(α-methyl-α-neopentyl-β-propiolactone) (80% poly-MNPL)/Poly (α-methyl-α-n-propyl-β-propiolactone) (20% MPPL) (1.1 g) was dissolved in Texanol ® (8.9 g). (poly-MNPL can also be named methyl neopentyl 3E polymer.)

(E) Elvacite ® 2041 (1.1 g) was dissolved in diethylene glycol monobutyl ether acetate (DGMEA) (8.9 g).

Five pastes were prepared as shown in Table 3.

TABLE 3

| | Paste Compositions | | | | |
|---|---|---|---|---|---|
| Paste | 1 | 2 | 3 | 4 | 5 |
| Glass Frit | 8.66 g | 8.66 g | 8.66 g | 8.66 g | 8.66 g |
| Calcined Alumina | 4.87 | 4.87 | 4.87 | 4.87 | 4.87 |
| Quartz | 1.77 | 1.77 | 1.77 | 1.77 | 1.77 |
| Binder A | 1.86 | | | | |
| Binder B | | 1.86 | | | |
| Binder C | | | 1.86 | | |
| Binder D | | | | 1.86 | |
| Binder E | | | | | 1.86 |
| Texanol ® | 2.00 | 3.00 | 3.00 | 2.50 | |
| DGMEA | | | | | 3.00 |

Each of the above paste compositions was printed on alumina substrates and fired at 600° C. in a belt furnace under nitrogen for 45 minutes. The fired parts were scraped off and analyzed for carbon. The results are shown in Table 4.

TABLE 4

Residual Carbon in Composition

| Sample | Polymer in Composition | Carbon (ppm) |
|---|---|---|
| 1 | Ethyl Cellulose N-22 | 1430 |
| 2 | Ethyl Cellulose N-50 | 1340 |
| 3 | MPPL | 900 |
| 4 | poly-MNPL (80%)/MPPL (20%) | 730 |
| 5 | Elvacite ® 2041 | 1150 |
| Blank | None, Inorganics Only | 360 |

EXAMPLE 16

Carbon Analysis of Degraded 3E Polymers 1. 100 mg of poly(methyl-propyl-lactone) in a helium atmosphere at atmospheric pressure was heated from 60° C. to 400° C. at a rate of 10° C./minute and held at 400° C. for 10 hours. The oxygen concentration throughout the experiment was <20 ppm. Carbon analysis showed 0.013 mg of residual carbon indicating 130 pmm (relative to initial polymer) carbon formation under these conditions.

2. 100 mg of poly(methyl-propyl-lactone) in a helium atmosphere at atmospheric pressure was heated from 60° C. to 600° C. at a rate of 10° C./minute and held at 600° C. for 30 minutes. The oxygen concentration throughout the experiment was <20 ppm. Carbon analysis showed 0.024 mg of residual carbon indicating 240 pmm (relative to initial polymer) carbon formation under these conditions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A binder composition consisting essentially of a mixture of at least two polymers of a 3-hydroxypropionic acid disubstituted at the 2-position by alkyl or hydrocarbon aryl or both, said composition having a glass transition temperature in the range of −30° C. to −40° C. being substantially to completely amorphous, displaying no crystalline exotherm in differential scanning calorimetry in a temperature range of −100° C. to +150° C. and volatilizing substantially cleanly at below 400° C. leaving a low carbon residue.

2. A binder composition according to claim 1, being completely amorphous.

3. A binder composition according to claim 1, consisting essentially of at least one copolymer of the disubstituted 3-hydroxypropionic acid.

4. A solution comprising an organic solvent having dissolved therein a binder composition according to claim 1.

5. A composition according to claim 1, consisting essentially of a plasticizer which is other than said polymers.

6. A slip composition comprising a solvent, particulate ceramic material, and dissolved in said solvent a binder composition according to claim 1.

7. A binder composition according to claim 1, wherein said mixture of polymers comprises different recurring units of

wherein:
$R^1$ is $C_{1-4}$-alkyl or phenyl; and
$R^2$ is $C_{1-5}$-alkyl or phenyl.

8. A composition according to claim 7, wherein $R_2$ is n-propyl or neopentyl.

9. A binder composition according to claim 7, comprising a mixture of said polymers, at least one being an oligomer having an average molecular weight of less than 5,000 and at least one having an average molecular weight of at least 10,000.

10. A binder composition according to claim 7, wherein said mixture of polymers is a methyl propyl/methyl-neopentyl/methyl ethyl terpolymer.

11. A binder composition according to claim 7, wherein said mixture of polymers is terminated by a deprotonated carboxylic terminal group.

12. A binder composition according to claim 11, wherein said deprotonated carboxylic terminal group is tetrabutyl phosphonium.

13. A copolymer of different recurring units of —(CH$_2$CR$^1$R$^2$COO)—, wherein $R^1$ is $C_{1-4}$-alkyl or phenyl and $R^2$ is $C_{1-5}$-alkyl or phenyl, said copolymer exhibiting no crystalline exotherm in differential scanning caloimetry in a temperature range of −100° C. to +150° C., and a glass transition temperature of below 40° C.

14. A copolymer according to claim 13, wherein said copolymer is a methyl propyl/methyl neopentyl/methyl ethyl terpolymer.

15. A ceramic slip or paste composition comprising particulate ceramic material, a solvent, a non-polylactone binder and an amount of a polymer sufficient to improve slip dispersion of said composition, said polymer comprising recurring units of the formula:

wherein:
$R^1$ is $C_{1-4}$-alkyl or phenyl; and
$R^2$ is $C_{1-5}$-alkyl or phenyl.

16. A ceramic composition comprising particulate ceramic material and a binder composition consisting essentially of a polymer of a 3-hydroxypropionic acid disubstituted at the 2-position by alkyl or hydrocarbon aryl or both, said binder having a glass transition temperature of −30° C. to +40° C., being substantially to completely amorphous, and volatilizing substantially cleanly at below 400° C., leaving a low carbon residue.

17. A shaped ceramic article of a composition of claim 16, wherein the ceramic article is in the unfired, green form.

18. A shaped article according to claim 17, wherein the shape is a ceramic tape.

19. An article of manufacture comprising the tape of claim 18 on a substrate.

20. A compound which is 2-methyl-2-neopentyl-3-acetoxypropionic acid or 2-methyl-2-neopentyl-3-hydroxypropionic acid.

* * * * *